US011772126B2

United States Patent
Shah et al.

(10) Patent No.: US 11,772,126 B2
(45) Date of Patent: Oct. 3, 2023

(54) SYSTEMS AND METHODS FOR DELIVERING THERAPEUTIC AGENTS

(71) Applicant: TheraDep Technologies, Inc., Palo Alto, CA (US)

(72) Inventors: Apoorva Shah, Burlington, MA (US); Liam O'Neill, Midleton (IE); Patrick Burt, Palo Alto, CA (US); John O'Donoghue, County Waterford (IE)

(73) Assignee: THERADEP TECHNOLOGIES INC., Palo Alto, CA (US)

( * ) Notice: Subject to any disclaimer, the term of this patent is extended or adjusted under 35 U.S.C. 154(b) by 968 days.

(21) Appl. No.: 16/074,365

(22) PCT Filed: Jan. 31, 2017

(86) PCT No.: PCT/US2017/015805
§ 371 (c)(1),
(2) Date: Jul. 31, 2018

(87) PCT Pub. No.: WO2017/136334
PCT Pub. Date: Aug. 10, 2017

(65) Prior Publication Data
US 2021/0187545 A1    Jun. 24, 2021

Related U.S. Application Data

(60) Provisional application No. 62/289,545, filed on Feb. 1, 2016.

(51) Int. Cl.
| | | |
|---|---|---|
| B05D 1/00 | (2006.01) | |
| A61B 18/04 | (2006.01) | |
| A61L 27/28 | (2006.01) | |
| A61L 27/54 | (2006.01) | |
| A61L 29/08 | (2006.01) | |
| A61L 29/16 | (2006.01) | |
| A61L 31/08 | (2006.01) | |
| A61L 31/16 | (2006.01) | |
| A61N 1/44 | (2006.01) | |
| B01L 3/00 | (2006.01) | |
| B05D 3/02 | (2006.01) | |
| B05D 3/14 | (2006.01) | |
| B05D 7/00 | (2006.01) | |
| A61B 18/00 | (2006.01) | |

(52) U.S. Cl.
CPC .............. *B05D 1/62* (2013.01); *A61B 18/042* (2013.01); *A61L 27/28* (2013.01); *A61L 27/54* (2013.01); *A61L 29/08* (2013.01); *A61L 29/16* (2013.01); *A61L 31/08* (2013.01); *A61L 31/16* (2013.01); *A61N 1/44* (2013.01); *B01L 3/5085* (2013.01); *B05D 3/0254* (2013.01); *B05D 3/145* (2013.01); *B05D 7/54* (2013.01); *A61B 2018/00589* (2013.01); *A61L 2420/02* (2013.01); *B01L 2200/12* (2013.01)

(58) Field of Classification Search
CPC .... B32B 5/16; B05D 1/62; B05D 3/00; A61L 29/16; A61L 31/16; G01N 33/48; H01L 21/26; A61C 5/06; A61C 5/50
See application file for complete search history.

(56) References Cited

U.S. PATENT DOCUMENTS

| | | | |
|---|---|---|---|
| 4,929,319 A | 5/1990 | Dinter et al. | |
| 6,565,558 B1 | 5/2003 | Lindenmeier et al. | |
| 7,201,935 B1 | 4/2007 | Claude et al. | |
| 7,455,892 B2 | 11/2008 | Goodwin et al. | |
| 8,771,782 B2 * | 7/2014 | O'Neill | A61L 29/14 |
| | | | 427/2.1 |
| 9,116,144 B2 * | 8/2015 | Naqvi | A61L 27/50 |
| 2002/0020024 A1 | 2/2002 | Schmitz et al. | |
| 2003/0087985 A1 | 5/2003 | Hubbell et al. | |
| 2004/0176749 A1 | 9/2004 | Lohmann et al. | |
| 2006/0084158 A1 | 4/2006 | Viol | |
| 2006/0147545 A1 * | 7/2006 | Scarborough | A61K 35/32 |
| | | | 424/549 |

(Continued)

FOREIGN PATENT DOCUMENTS

| | | |
|---|---|---|
| EP | 1498128 A1 | 1/2005 |
| EP | 1705965 A1 | 9/2006 |

(Continued)

OTHER PUBLICATIONS

Qu et al., Silver/hydroxyapatite composite coatings on porous titanium surfaces by sol-gel method, Oct. 2010, Journal of Biomaterials Research B. pp. 40-48 (Year: 2010).*

(Continued)

*Primary Examiner* — Dah-Wei D. Yuan
*Assistant Examiner* — Andrew J Bowman
(74) *Attorney, Agent, or Firm* — Bookoff McAndrews, PLLC

(57) ABSTRACT

Plasma systems for depositing biomolecules, pharmaceutical agents, and other therapeutic active agents onto surfaces are described. The systems may include a plasma device having one or more electrodes, a gas supply inlet, a plasma outlet exposed to ambient pressure, and an ignition system operatively connected to the electrodes for providing a non-thermal equilibrium plasma within the plasma chamber. A particulate delivery system may be used to introduce the active agent(s) as a dry powder into or downstream of the plasma, and to deposit the plasma-treated active agent(s) to produce a coating on a surface. The coating may retain the activity of the active agent(s).

20 Claims, No Drawings

(56) References Cited

U.S. PATENT DOCUMENTS

| | | | |
|---|---|---|---|
| 2007/0029500 A1 | 2/2007 | Coulombe et al. | |
| 2008/0118734 A1 | 5/2008 | Goodwin et al. | |
| 2008/0199513 A1 | 8/2008 | Beretta et al. | |
| 2008/0237484 A1 | 10/2008 | Morfill et al. | |
| 2011/0039355 A1* | 2/2011 | Zhao | H01J 37/3244 257/E21.528 |
| 2011/0159273 A1* | 6/2011 | Lukowski | A61L 27/34 428/323 |
| 2012/0009231 A1 | 1/2012 | Herbert et al. | |
| 2012/0089084 A1 | 4/2012 | O'Keeffe et al. | |
| 2012/0171354 A1* | 7/2012 | O'Neill | A61L 27/34 427/2.24 |
| 2015/0111170 A1* | 4/2015 | Guy, Sr. | A61B 18/042 604/24 |
| 2015/0314036 A1 | 11/2015 | O'Keeffe et al. | |
| 2018/0154039 A1 | 6/2018 | O'Keeffe et al. | |
| 2019/0126027 A1 | 5/2019 | O'Neill et al. | |

FOREIGN PATENT DOCUMENTS

| | | |
|---|---|---|
| EP | 2666544 A1 | 11/2013 |
| JP | 2008-501069 | 5/2005 |
| JP | 2006-501356 | 1/2006 |
| JP | 2008-515511 | 5/2008 |
| WO | WO 89/01790 | 3/1989 |
| WO | WO 98/22153 | 5/1998 |
| WO | WO 2002/028548 A2 | 4/2002 |
| WO | WO 2003/097245 A2 | 11/2003 |
| WO | WO 2004/031266 A2 | 4/2004 |
| WO | WO 2005/106477 A2 | 11/2005 |
| WO | WO 2005/110626 A2 | 11/2005 |
| WO | WO 2006/038056 A1 | 4/2006 |
| WO | WO 2006/048650 A1 | 5/2006 |
| WO | WO 2006/116252 A2 | 11/2006 |
| WO | WO 2007/106212 A1 | 9/2007 |
| WO | WO 2009/101143 A1 | 8/2009 |
| WO | WO 2009/146432 A1 | 12/2009 |
| WO | WO 2010/002287 A1 | 3/2010 |
| WO | WO 2010/105829 A1 | 9/2010 |
| WO | WO 2010/146438 A1 | 12/2010 |
| WO | WO 2012/080835 A2 | 6/2012 |

OTHER PUBLICATIONS

R1, LBR Hardness Melting Plot, Feb. 2008, Some Fundamentals of Mineralogy and Geochemistry, p. 1 (Year: 2008).*

Bogaerts et al., "Gas Discharge Plasmas and Their Applications," *Spectrochimica Acta Part B*, vol. 57, pp. 609-658 (2002).

Department of Defense, Blast Injury Research Program Coordinating Office, "Minimizing the Impact of Wound Infections Following Blast-Related Injuries," 2016.

Fridman et al., "Blood Coagulation and Living Tissue Sterilization by Floating-Electrode Dielectric Barrier Discharge in Air," Plasma Chem Plasma Process, 26: 425-442 (2006).

Fridman et al., "Comparison of Direct and Indirect Effects of Non-Thermal Atmospheric-Pressure Plasma on Bacteria," *Plasma Processes and Polymers*, vol. 26: pp. 370-375 (2007).

Guerin et al., "Plasma Polymerization of Thin Films: Correlations Between Plasma Chemistry and Thin Film Character," *Langmuir*, vol. 18 pp. 4118-4123 (2002).

Heinlin et al. "Plasma Medicine: Possible Applications in Dermatology," *Journal of the German Society of Dermatology*, 8, pp. 1-9 (2010).

International Search Report in priority application PCT/IB10/01439, dated Nov. 16, 2010 (2 pages).

Ladwig et al., "Atmospheric Plasma Deposition of Glass Coatings on Aluminum," *Surface & Coatings Technology*, vol. 201, pp. 6460-6464 (2006).

Laroussi, Mounir, "Plasma Medicine: A Brief Introduction," Plasma, 1, pp. 47-60 (2018).

Lloyd et al. "Gas Plasma: Medical Uses and Developments in Wound Care," Plasma Processes and Polymers, 7, pp. 194-211 (2010).

Massarweh et al., "Electrosurgery: History, Principles, and Current and Future Uses", *J. Am. Coll. Surg.*, vol. 202, pp. 520-530 (2006).

Mennel et al., "Helium (Argon) Plasma Coagulation in Neurosurgery. Morphology of Tissue Damage and Reparation," *Exp Toxic Pathol*, vol. 54, pp. 255-263 (2002).

Okazaki et al., Appearance of Stable Glow Discharge In Air, Argon, Oxygen and Nitrogen At Atmospheric Pressure Using A 50 Hz Source,, *J. Phys. D; Appl. Phys.* vol. 26, pp. 889-892 (1993).

Reich et al., "Argon Plasma Coagulation (APC) for Endo-Urological Procedures: Ex-Vivo Evaluations of Hemostatic Properties," *European Urology*, vol. 44, pp. 272-276 (2003).

Roth et al., "Atmospheric Pressure Plasma Sources," Ch. 15, pp. 37-73 in Industrial Plasma Engineering, vol. 2: Applications to Non-thermal Plasma Processing, Institute of Physics Publishing (2001).

Shoulders et al., "Collagen Structure and Stability," *Annu. Rev. Biochem*, vol. 78, pp. 929-959 (2009).

Supplementary European Search Report for European Application No. 10789079, dated Aug. 22, 2014 (1 page).

International Search Report in PCT/US2017/015805 dated Jun. 26, 2017 (6 pages).

Bulina et al., "A Study of Thermal Stability of Hydroxyapatite," *Minerals*, vol. 11, 1310 (2021).

* cited by examiner

SYSTEMS AND METHODS FOR DELIVERING THERAPEUTIC AGENTS

CROSS-REFERENCE TO RELATED APPLICATIONS

This application is a U.S. National Stage filing under 35 U.S.C. § 371 of International Patent Application No. PCT/US2017/015805, filed on Jan. 31, 2017, which claims benefit of priority to U.S. Provisional Application No. 62/289,545 filed on Feb. 1, 2016, which is incorporated by reference herein in its entirety.

BACKGROUND

In general, there are two plasma types, namely thermal equilibrium and non-isothermal equilibrium plasmas. Thermal equilibrium plasmas are typically hot with temperatures ~10,000 K and are used in industry as plasma torches, jets and arcs for welding. These hot plasma systems are also used in thermal spray coating where they can be used to deposit metallic and ceramic coatings onto metal surfaces for applications as diverse as producing biocompatible hydroxyapatite coatings on medical implants to the deposition of protective coatings on gas turbine components. Despite the widespread use of thermal plasmas, their applications are limited by the high thermal energy within plasma devices which prevent these devices from depositing temperature sensitive materials such as proteins, polysaccharides and other chemical compounds and biomaterials.

In contrast, non-isothermal plasmas are generally cool and can be employed in manufacturing processes including surface cleaning (including, e.g., removal of unwanted substances such as contaminants), etching (e.g., removal of bulk substrate material), activation (e.g., changing surface energies) and deposition of functional thin film coatings onto surfaces. Historically, these coating devices were limited to vacuum conditions and used only gas phase precursors to produce coatings. As a result, the chemistry of the deposited materials was inherently simplistic and these devices were not compatible with large, high molecule weight macromolecules.

However, plasma systems such as these have been widely used to modify surfaces to allow for subsequent attachment of biomolecules through traditional wet chemistry techniques. Such a biomolecule attachment technique relies on the use of plasma activation as part of a multistep process in which a plasma is first used to clean and activate the substrate surface. Linker chemicals may then be deposited using either plasma deposition or standard wet chemical techniques. Finally, the target biomolecules are then attached to the surface using wet chemistry. Alternatively, plasma systems have been used to deposit coatings on to which biomolecules can be subsequently attached in another wet chemical multistep process. Either way, complex linkers and binder chemicals are required to prepare the surface in advance of introducing the target biological molecule.

Recent years have seen the development of plasma devices that operate at atmospheric pressure and which can also produce functional coatings using gas phase monomers. However, the switch from vacuum systems to ambient pressure also allows for the use of precursors other than gas phase monomers in the production of thin films. U.S. Pat. No. 4,929,319 discloses a process for treating a plastic substrate in which a liquid aerosol is introduced into an atmospheric corona discharge while a flat plastic substrate is passed through the corona discharge operating in open air.

U.S. Pat. No. 7,455,892 discloses a method for producing a coating wherein a polymer forming material is atomized into a homogeneous atmospheric pressure plasma glow discharge in order to produce a polymeric coating on a substrate. The list of potential monomers disclosed includes materials which are known to polymerise under exposure to free radicals or UV radiation to produce a coating. These precursors typically contain vinyl, cyclic or other reactive groups.

WO 2007/106212 discloses a plasma system which combines an atmospheric pressure plasma device coupled to a vacuum deposition chamber in order to deposit a biomolecule on a surface. The idea of combing vacuum chambers and atmospheric pressure plasma jets into one system represents a complex engineering challenge. Furthermore, exposing a biomolecule to vacuum can result in molecular damage, denaturation, and loss of functionality.

Argon plasma coagulation (APC) is a technique used in medicine wherein a high energy argon plasma is used to alter tissue through a combination of protein coagulation and tissue dehydration. Under standard use, APC produces denatured and charred surfaces and is not used for deposition of controlled surface chemistries. WO 02/28548 describes a process in which an aerosol is introduced into an atmospheric pressure glow discharge (APGD) plasma and a coating is thereby formed on a substrate.

WO 2005/110626 describes the use of a non-thermal plasma device to convert a liquid aerosol containing an active agent and a reactive monomer into a dry coating which contains both a polymer (produced by polymerising the reactive monomer) and the active agent which is physically entrapped in the polymer coating. Similarly, WO 2005/106477 describes an atmospheric pressure non thermal plasma process that involves the introduction of reactive monomers and active agents into the plasma to produce a polymerised coating of the reactive monomer which entraps the active agent.

The requirement to induce reactions within the polymer precursor without damaging the active agent limits the types of molecules that can undergo controlled polymerisation in a plasma without loss of functionality. Typically, this requires the reactive precursor to contain a vinyl or cyclic structure, which can be preferentially reacted in the plasma. If molecules do not possess such functional groups, then they can be polymerised via bond breakage and fragmentation in other areas of the molecule, which can give rise to chemical alterations and loss of functionality. Some researchers have attempted to work around this limitation by chemically altering the molecule, e.g., adding reactive chemical functionality to the molecule. However, the resultant coating may lose some activity of the active agent and/or produce unforeseen consequence in clinical settings requiring detailed safety studies before such modified materials could be safely used in humans. The requirement to chemically modify the molecule also can increase the overall complexity and cost of the process. Furthermore, these types of processes require the active agent to be dissolved in a solvent, which may limit the applicability of these techniques. For example, the molecule may be partially or complete insoluble, or may require the use of organic solvents which are known to undergo plasma polymerization reactions and may therefore co-polymerise alongside the molecule, resulting in a coating that contains additional unwanted materials. These materials may produce negative biological reactions. For example, many biomolecules are biologically active due to their unique shape or conformation, wherein thermal energy can cause denaturation to render them inactive. Many pharmaceutical products suffer from similar limitations and cannot be directly exposed to plasma due to a loss of activity caused by chemical and/or conformational changes.

As a result, researchers often have avoided intentional exposure of biomolecules to plasma sources as the thermal, electrical, UV and other active species within the plasma can induce irreversible chemical and/or conformation changes that would destroy the biological/pharmaceutical activity of the molecule.

SUMMARY

The present disclosure includes methods of producing a coated substrate. For example, the method may comprise introducing a plurality of dry particles into a non-thermal plasma, each particle comprising at least one active agent chosen from biomolecules, pharmaceutical agents, or combinations thereof; and exposing a substrate to the plurality of dry particles and the plasma to deposit a coating comprising the at least one active agent onto the substrate. The active agent(s) may have therapeutic biological activity and/or therapeutic pharmaceutical activity. In some examples, the plurality of dry particles may be introduced into an afterglow portion of the plasma.

According to some aspects of the present disclosure, each particle consists of only the at least one active agent, e.g., wherein the dry particles do not contain reactive monomers or chemical components that induce polymerization of the active agent(s). In some examples, the active agent(s) may be cross-linked. The coating may retain at least a portion of, or the entirety of, the biological or pharmaceutical activity of the at least one active agent prior to deposition onto the substrate to form the coating. In at least one example, the coating comprises at least one biomolecule and/or at least one antibiotic agent.

Exemplary substrates may include, for example, external tissue, internal tissue, a diagnostic component, a medical device, or a food product. In at least one example, the substrate comprises a multi-well plate and the at least one active agent comprises a biomolecule. In other examples, the substrate comprises an implantable medical device. In yet other examples, the substrate comprises external tissue and/or internal tissue, including, e.g., wounded, diseased, or injured tissue.

According to some aspects of the present disclosure, the coating comprises at least one first layer comprising a pharmaceutical agent and at least one second layer comprising a biomolecule. The first layer(s) may be adjacent to the second layer(s) and/or the coating may comprise one or more first layers between one or more second layers. In some examples, the first layers and/or second layers may have a thickness ranging from 10 nm to 500 nm, such as from 50 nm to 150 nm, from 10 nm to 100 nm, from 75 nm to 250 nm, or from 300 nm to 500 nm. For example, the total thickness of the coating comprising the first layer(s) and the second layer(s) may range from about 20 nm to 1 µm or more.

The coating may comprise a single active agent or two or more active agents. In at least one example, the at least one active agent comprises a first active agent and a second active agent, and introducing the plurality of dry particles into the plasma comprises introducing the first active agent into a different portion of the plasma than the second active agent, wherein the first active agent is a biomolecule and the second active agent is a pharmaceutical agent.

The present disclosure further includes a method of producing a coated substrate, comprising: applying at least one active agent to a surface of a substrate, the at least one active agent being chosen from biomolecules, pharmaceutical agents, or combinations thereof; and exposing the surface of the substrate to an afterglow of a plasma to form a dry coating comprising the at least one active agent.

Applying the at least one active agent may include forming a uniform layer of the at least one active agent on the surface of a substrate. In some examples, the at least one active agent is applied as a dry solid. In some examples, the at least one active agent is applied to the surface of the substrate in solution with at least one solvent, and the surface of the substrate is dried prior to exposure to the plasma. As mentioned above and elsewhere herein, exemplary substrates include tissue (e.g., external tissue and/or internal tissue, including wounded, diseased, or injured tissue), diagnostic components, medical devices, and food products. The dry coating thus formed may retain at least a portion of, or an entirety of, the biological or pharmaceutical activity of the at least one active agent.

The present disclosure further includes a method of producing a coated substrate, comprising exposing a substrate to the pharmaceutical agent and a plasma to deposit at least one first layer comprising the pharmaceutical agent onto the substrate, wherein the at least one first layer retains a pharmaceutical activity of the pharmaceutical agent; and exposing the substrate to a biomolecule and the plasma to deposit at least one second layer comprising the biomolecule onto the substrate, wherein the at least one second layer is adjacent to the at least one first layer; wherein the at least one first layer retains a pharmaceutical activity of the pharmaceutical agent, and the at least second layer retains a biological activity of the biomolecule. At least one of the pharmaceutical agent or the biomolecule may, for example, be introduced into the plasma (e.g., an afterglow or afterglow region of the plasma) in the form of dry particles.

According to some aspects of the present disclosure, the at least one first layer comprises a plurality of first layers having a total thickness ranging from 10 nm to 500 nm, such as from 50 nm to 150 nm, from 10 nm to 100 nm, from 75 nm to 250 nm, or from 300 nm to 500 nm. Additionally or alternatively, the at least one second layer may comprise a plurality of second layers having a total thickness ranging from 10 nm to 500 nm, such as from 50 nm to 150 nm, from 10 nm to 100 nm, from 75 nm to 250 nm, or from 300 nm to 500 nm. In some examples, the total thickness of the coating comprising the plurality of first layers and the plurality of second layers may range from 20 nm to 1 µm or more, e.g., a total coating thickness ranging from 50 nm to 800 nm, from 100 nm to 500 nm, from 250 nm to 750 nm, from 300 nm to 500 nm. For example, the total thickness of the coating may be about 50 nm, about 100 nm, about 150 nm, about 250 nm, about 300 nm, about 500 nm, about 750 nm, about 800 nm, about 900 nm, about 1 µm, or greater than 1 µm.

As mentioned above and elsewhere herein, exemplary substrates include tissue (e.g., external tissue and/or internal tissue, including wounded, diseased, or injured tissue), diagnostic components, medical devices, and food products. In at least some examples, the plasma may have greater power during exposure of the substrate to the biomolecule and the plasma than exposure of the substrate to the pharmaceutical agent and the plasma.

Also disclosed herein are devices comprising a coating as described in the summary above and the following description, e.g., the coating comprising at least one active agent such as a biomolecule, a pharmaceutical agent, or a combination thereof. For example, the device may comprise a diagnostic component or a medical device.

DETAILED DESCRIPTION

The present disclosure includes systems, devices, and methods for delivering active therapeutic agents (e.g., biomolecules, pharmaceutically active agents, and/or combinations thereof) to a surface (e.g., a tissue surface or non-tissue substrate). The term "biomolecule" as used herein generally refers to molecules present in living organisms (including, e.g., molecules involved in metabolic processes), including, but not limited to, large macromolecules such as proteins, carbohydrates, lipids, and nucleic acids, as well as small molecules such as primary metabolites, secondary metabolites, and natural products. The deposited coating(s) may comprise mixtures or combinations of different active agents, e.g., mixtures of different biomolecules and/or pharmaceutical agents. In some examples, one or more of the active agents, or all of the active agents of the coating, do not contain vinyl groups.

Plasmas can offer a number of advantages for coating deposition. The combination of reactive plasma and chemically-active monomers may produce a coating that is uniform, pin hole free, and/or well bonded to the substrate. Furthermore, curing of coating materials may occur in a manner that is almost instantaneous, which may offer processing advantages.

The methods herein may be used to deposit one or more active agents onto external or internal tissue, or onto another substrate surface such as a medical device or diagnostic component. Exemplary medical devices include, but are not limited to, scalpels, clamps, needles, and medical implants such as stents, catheters, ports, expandable balloons, prosthetic implants, orthopedic implants, dental implants, cochlear implants, ear tubes, implantable mesh, spinal cages, maxillofacial implants, scaffolding (e.g., for tissue regeneration or grafting), pulse generators, valves, hormone delivery implants, skin grafts, bone grafts, artificial eye lenses, contact lens, hearing aids, breast implants, trauma fixation devices, screws, plates, rods, pins, nails, needles, biosensors, sensory implants, neural implants, pacemakers, defibrillators, electrodes, subcutaneous implants including drug delivery implants, cosmetic implants, hip implants and knee replacement implants, blood dialysis equipment, ventilators and associated tubes. Exemplary diagnostic components include, but are not limited to, multi-well plates, glass slides, pipettes and pipette tips, sample containers, glucose monitors, biosensors, enzyme biochips, affinity biochips, chemical sensors, pathogen sensors, contaminant sensors, diagnostic biochips, blood pressure monitors, ELISA test components, and other diagnostic components.

In some aspects, the present disclosure provides a plasma system or device designed to produce a non-thermal equilibrium or cold plasma. To achieve this, for example, the plasma may be powered at a frequency of at least 10 kHz, such as greater than 20 kHz, for example greater than 125 kHz. The maximum frequency may be less than 1 MHz, such as less than 900 kHz, for example less than 750 kHz.

In at least one aspect, the plasma is a pulsed plasma. The plasma may be pulsed at various duty cycles such that the power delivered is less than 100 W, such as less than 20 W, e.g., less than 10 W. The pulsing may be such that the applied power is off for at least 50% of the time, e.g., with the pulses switched on and off many times per second. For example, the plasma may be pulsed on and off to deliver an on-time ranging from about 1 nanosecond (ns) to about 500 milliseconds (ms). For example, the plasma may be pulsed with an on-time ranging from 1 ms to 500 ms, such as from 10 ms to 300 ms, from 50 ms to 100 ms, e.g., an on-time of about 1 ms, about 10 ms, about 50 ms, about 75 ms, about 100 ms, about 200 ms, about 250 ms, about 300 ms, about 400 ms, or about 500 ms. In some aspects of the present disclosure, the plasma may be pulsed with an on-time ranging from 1 ns to 500 ns, such as from 10 ns to 300 ns, 50 ns to 100 ns, e.g., an on-time of about 1 ns, about 10 ns, about 50 ns, about 75 ns, about 100 ns, about 200 ns, about 250 ns, about 300 ns, about 400 ns, or about 500 ns. For example, for the treatment of tissue, such as cancerous tissue, the plasma may be a nano-second or pico-second pulsed plasma. In these examples, the plasma may be only turned on for fractions of a millisecond for each pulse, e.g. less than 500 ns or less than 100 ns.

The systems herein may include a plasma device comprising one or more electrodes and an ignition system operatively connected to the electrodes for providing a non-thermal equilibrium plasma. The plasma device may further comprise a gas supply inlet and a plasma chamber exposed to ambient pressure, wherein the non-thermal equilibrium plasma may be generated within the plasma chamber.

In at least one embodiment, the plasma device is a plasma coagulation device and the plasma produced by the device is introduced into a chamber alongside at least one biomolecule and/or at least one pharmaceutical. An end of the chamber may be open to atmosphere, and the substrate (e.g., a surface of a medical device or other object, or a soft tissue surface, such as a wound) to be treated is placed adjacent to the exit. This may result in plasma-treated materials depositing on the surface of the substrate as a coating. Although plasma coagulation devices are thought to be destructive under normal operating conditions, when operated at low power in the configurations described herein, the power and heat delivered may be significantly reduced and active agent(s) of the coatings may retain their therapeutic efficacy (e.g., biological activity and/or pharmaceutical activity). The gas used to generate the plasma may comprise, e.g., helium or argon. For example, the device may comprise an argon plasma coagulator. In some embodiments, a helium plasma coagulator may be used, e.g., in place of the argon coagulator.

In a further aspect, there is provided a non-thermal plasma-treated biomolecule or non-thermal plasma-treated pharmaceutically active agent for use in coating a substrate such as a soft tissue surface (e.g., a wound) or other surface, such as a hard surface (e.g., a medical device). The coatings herein may be applied to human and/or non-human animal tissue.

The methods disclosed herein may eliminate the need to employ solvents in the process and/or produce coatings that are biologically and/or pharmaceutically active.

In some embodiments, the active agent(s) (e.g., biomolecule(s) and/or pharmaceutically active agent(s)) may be introduced into the plasma in the form of dry particles (e.g., a dry powder). Without being bound by theory, in the case of dry particles of active agents, it is believed that the plasma may activate the outer surface or outermost layer(s) of each particle, thereby facilitating cross-linking of the particulate materials to bind the particles to each other and to an adjacent target surface, whereas the bulk of the material contained within the dry particles (e.g., within the activated outer layer(s)) is protected from the reactive species present in the plasma. Also, without being bound by theory, it is believed that the thermal energy of the plasma may be sufficient to at least partially melt the outermost layer(s) of the particle, thereby facilitating adjacent particles solidifying into a continuous layer on a substrate surface (e.g., a medical device or other object, or a soft tissue surface). Thus, the biological/pharmaceutical activity of the powder may be retained. According to some aspects of the present disclosure, the coating may consist of or consist essentially of the active agent(s). That is, no additional polymer forming materials in addition to the active agent(s) may be required, such that the coating may be formed of greater than 99%, e.g., 100%, pure active material(s). According to some aspects of the present disclosure, the dry particles may be introduced into the plasma as the dry particulate material(s), wherein no solutions or liquids may be required to protect the active material(s) from the plasma.

The methods disclosed herein include delivering active agents (e.g., organic molecules such as active pharmaceutical agents and/or biomolecules) in the form of dry particles to a substrate surface. Many biomolecules and other organics are generally soft and deformable, such that they may be activated and attached to surfaces, e.g., as at least some of these materials inherently deform and stick to a target surface. Without being bound by theory, it is believed that the activation of such molecules may include ionic charging, which may result in electrostatic bond formation or ionic bonding. For example, in some embodiments of the present disclosure, exposure of the substrate and/or active agent(s) to plasma may lead to oxidation at the surface of the substrate and/or activation of the particles of the active agent(s). Such oxidation may result in the formation of polar functional groups on the surfaces of the substrate and/or active agent(s) that can partake in bonding, e.g., formation of polar covalent bonds. Furthermore, without being bound by theory, it is believed that the presence of free radicals in the plasma may result in the formation of free radicals on the surface of the particles of the active agent(s) and the substrate surface, which can produce covalent bonding.

Active agents suitable for introduction to the plasma in the form of dry particles may have a melting point less than about 100° C., e.g., a melting point ranging from 60° C. to 100° C., from 75° C. to 100° C., from 85° C. to 100° C., from 75° C. to 95° C., or from 90° C. to 100° C. Additionally or alternatively, the active agents suitable for introduction to the plasma may have a Mohs hardness less than about 3, e.g., a Mohs hardness ranging from 1 to 3. For example, the active agent(s) may have a Mohs hardness of about 1, about 2, or about 3. In at least one embodiment, the active agent(s) being introduced into the plasma as dry particles have a melting point less than 100° C. and a hardness less than 3 on the Mohs scale. In some embodiments, the active agent(s) do not include harder inorganic materials or ceramic biomolecules such as hydroxyapatite, calcium phosphates, or other biominerals with a Mohs hardness greater than 3, greater than 4, or greater than 5.

In at least one embodiment, the plasma and active agent(s) in dry particulate (powder) form interact within a plasma chamber having an open end or exit, e.g., such that the active agent(s) may be activated by the plasma. The plasma chamber may contain an inert gas or mixture of gases. A substrate may be placed adjacent to the open end of the plasma chamber to allow the activated material(s) deposit onto the surface of the substrate adjacent to the exit of the chamber. This may allow the activation to occur in a region that is predominantly filled with the inert gas or gaseous mixture, such as nitrogen, helium, argon, or mixtures thereof. This method may be used, for example, for coating external wounds (e.g., damaged/injured tissue of a patient) and/or for coating devices such as medical devices and/or diagnostic components. Exemplary medical devices include, but are not limited to, scalpels, clamps, needles, and medical implants such as stents, catheters, ports, expandable balloons, prosthetic implants, orthopedic implants, dental implants, cochlear implants, ear tubes, implantable mesh, spinal cages, maxillofacial implants, scaffolding (e.g., for tissue regeneration or grafting), pulse generators, valves, hormone delivery implants, skin grafts, bone grafts, artificial eye lenses, contact lens, hearing aids, breast implants, trauma fixation devices, screws, plates, rods, pins, nails, needles, biosensors, sensory implants, neural implants, pacemakers, defibrillators, electrodes, subcutaneous implants including drug delivery implants, cosmetic implants, hip implants and knee replacement implants, blood dialysis equipment, ventilators and associated tubes. Exemplary diagnostic components include, but are not limited to, multi-well plates, glass slides, pipettes and pipette tips, sample containers, glucose monitors, biosensors, enzyme biochips, affinity biochips, chemical sensors, pathogen sensors, contaminant sensors, diagnostic biochips, blood pressure monitors, ELISA test components, and other diagnostic components.

The coating processes disclosed herein may be compatible with aseptic manufacturing techniques. For example, the active agent(s) may be sterilized using appropriate filtering, heating or other methods. Additionally or alternatively, the plasma may neutralize bacterial species or other adverse microbial species, e.g., further reducing bacterial numbers.

When treating internal tissue, such as a peptic ulcer or a tumour in the pancreas or other organ, the plasma and active agent(s) may be introduced into the body endoscopically, e.g., such that the plasma may activate the active agent(s) adjacent to the target tissue. The internal body space of the patient may provide a method to exclude air, such that no plasma chamber need be provided. Devices used for such internal treatment may be similar to the endoscopic plasma coagulator devices, together with a mechanism or system to deploy the active agent(s).

In some embodiments, one or more pharmaceutically active materials and/or biomolecules may be dissolved in a liquid to form a solution. A coating may then be formed by spraying the solution of the active agent(s) as an aerosol into a low energy, non-thermal equilibrium atmospheric pressure plasma and exposing the surface to be coated to the plasma and aerosol. This may result in the nebulized active agent(s) undergoing activation within the plasma and forming a dry coating of the active agent(s) on the substrate surface. For example, the coating may comprise coagulated active agent (s). This method may allow for pharmaceutical agents and/or biomolecules to be deposited onto a substrate surface without the use of binders, linkers, polymers, or other materials.

In some examples, the method may simultaneously produce a coating that is chemically bonded to the surface. The active agent(s) may be chemically bonded to the substrate surface with or without cross-linking of the active agent(s). In some examples, the active agent(s) are not polymerized in the coating. For example, one or more of the active agents, or all of the active agents of the coating, do not contain vinyl groups or other chemical functionalities that would be expected to undergo free radical style polymerization reactions.

In at least some aspects of the present disclosure, for example, the coating may comprise at least one material that is cross-linked. The cross-linked material(s) may be active agents and/or other materials such as polymers. Crosslinking may increase the strength and/or density of the coating, which may produce a controlled elution of active agent(s) of the coating. Depending on the materials of the coating and the degree of cross-linking, release of active agents from the coating (e.g., into adjacent tissues) may range from hours to days. In some examples, active agent(s) may elute from a coating having a thickness of less than 200 nm or less than 300 nm over a period of a few hours, e.g., from 1 hour to 8 hours, or from 3 hours to 5 hours. For example, a relatively thin coating of material (e.g., a thickness ranging from about 10 nm to 50 nm) on a substrate may elute over several hours (e.g., 1 hour to 5 hours). By increasing the coating thickness to 500 nm or more (e.g., from 500 nm to 1 µm, e.g., a thickness of 600 nm, 700 nm, 750 nm, 800 nm, 900 nm, 1 µm, or more than 1 µm), the active agent(s) may elute over a few days, e.g., from 1 day to 14 days, from 2 days to 10 days, or from 5 days to 7 days. The rate of release of the active agent from the coating may depend on the solubility of the active agent and/or the degree of crosslinking of the coating. For example, if the cross-linked density is increased, then the same thickness of coating may remain on the substrate surface for more than 1 day, e.g., up to 10 days, such as from 7 to 10 days, before the coating is enzymatically degraded.

The operating parameters of the plasma may be adjusted to control cross-linking of materials during deposition onto the substrate. For example, increasing the applied voltage generally increases the number of active species in the plasma, which can enhance cross-linking. As an example, coatings of active agents may be deposited using applied voltages of about 6 kV (peak to peak) at frequencies ranging from 10 kHz to 600 kHz with an applied duty cycle of 20%. Increasing the voltage to 7 kV to 10 kV may increase the degree of cross-linking, e.g., forming a more durable coating. Further, for example, increasing the duty cycle in a pulsed plasma system may enhance cross-linking. For example, the duty cycle may be increased by increasing the on-time or decreasing the off-time, e.g., to increase the duty cycle from about 20% to about 40%, about 45%, about 50%, about 55%, about 60%, about 65%, about 70%, about 75%, about 80%, or even continuous wave operation.

Without being bound by theory, it is believed that, in at least some cases and depending on the active agent(s), the deposition process does not involve polymerization of the material, but instead involves some cross-linking of the active agent(s) (in particulate or aerosol form) with additional formation of bonds to the activated substrate surface. This activation may begin when the material first contacts the plasma and may proceed as long as the material remains in contact with the plasma and/or species emanating from the plasma. Additionally or alternatively, the substrate may be also activated by the plasma and able to react with the active agent(s) to produce a well adhered coating. The degree of activation and bonding may be proportional to the energy of the plasma and/or the time the active agent(s) and/or substrate spent in contact with the plasma.

In some embodiments, the time spent by the active agent(s) within the plasma chamber may be less than 1 second, such as less than 0.5 seconds, e.g., from 0.1 second to 1 second or from 0.1 second to 0.5 second. Upon reaching the surface of the substrate, the material(s) may be exposed to further plasma energy, e.g., from long-lived particles or species that exit the plasma chamber. In effect, the plasma can be used to initiate coagulation and/or cross-linking of the active chemical/biochemical agents to form a coating or chemical binding of molecules (including, e.g., chemical binding of particles). Unexpectedly, it has been found that this process does not deactivate the biomolecules or cause decomposition of the pharmaceutical agents, such that and a high degree of activity can be retained in the resulting coating.

The deposited material(s) may be strongly bonded to the substrate or may form only a loose attachment, depending upon the nature of the substrate and the material(s), the operating parameters of the plasma (e.g., the level of plasma power employed), and the way in which the material(s) are exposed to the plasma. For example, in some embodiments, increasing the plasma power may increase the strength of cross-linking among active agent(s) and/or may enhance the strength of bonding to the surface, which may result in the formation of covalent bonding between adjacent particles or aerosols of the active agent(s) and/or covalent bonding of the active agent(s) to the substrate. Decreasing the plasma power may result in a relatively weaker type of bonding like hydrogen bonding, which is generally understood to be less strong than covalent bonding. Further decreasing the plasma power could then limit the interaction to other types of bonding, such as electrostatic or van der Waals attractions.

In some embodiments, the coating can be formed without the addition of film forming materials. For example, the coating may consist of or consist essentially of one or more active agents. There may be no requirement to add materials that undergo standard plasma induced free radical or ionic polymerization through reactive groups such as unsaturated bonds (e.g., double or triple bonds), cyclic ring structures, aromatic rings, peroxides, silanes, epoxides, or other reactive groups. Instead, the only material(s) introduced into the plasma for deposition onto the substrate may be the biomaterial and/or pharmaceutical active agent (s) (e.g., as precursor materials).

As discussed above, in some aspects of the present disclosure, directly introducing biomolecules and/or active pharmaceutical materials as a dry nebulized powder into a low energy atmospheric pressure or vacuum plasma produces a one-step route to the formation of stable, dry, adherent coatings which retain the biological or pharmaceutical activity of the starting material. Without being bound by theory, it is thought that the plasma may activate the surface of the particles of the active agent(s) to create reactive chemical sites that may react with the surface of other particles. For example, the plasma may contain free radicals which abstract atoms from the surface of the particles and thereby create a particle with a free radical moiety on its surface available to bond to adjacent particles and/or to a substrate surface. Similarly, plasma devices, including those operated at atmospheric pressure, may be capable of oxidizing the surface of a material and producing polar functional groups such as carboxyl, carbonyl, and hydroxyl groups, which can take part in hydrogen bonding. Also, plasmas are generally rich in charged ions and free electrons, and these species can produce reactive chemical sites on the surface of particles that can participate in ionic bonding. Additionally or alternatively, collisions with ions or free electrons may produce a positive or negative charge on the particles, which may result in electrostatic bonding to other surfaces.

The active agent(s) may be nebulized using any appropriate atomizer or nebulizer, including, e.g., ultrasonic, piezo, pneumatic, mechanical, electrical, vibrating mesh or jet nebulizers. In at least one embodiment, the active agent (s) (e.g., pharmaceutical agents and/or biomolecules) are entrapped as a solid (e.g., a powder) in or on a foam, mesh or fabric surface and gas is blown through the foam, mesh or fabric surface, thereby transporting the active agent to a target substrate surface. The average diameter of the powder particles may be less than 1000 μm, such as less than 100 μm, for example, less than 10 μm. For example, the average diameter of the dry particles may range from about 1 μm to about 10 μm, from about 5 μm to about 50 μm, from about 25 μm to about 75 μm, from about 50 μm to about 100 μm, from about 100 μm to about 200 μm, from about 250 μm to about 500 μm, or from about 500 μm to about 750 μm. The foam, mesh or fabric may be made from any suitable non-reactive material or combination of materials, such as a polymer or a metal. Such materials may be sufficiently permeable to allow the gas to permeate through and extract the powder particles for transportation to the surface.

The coatings may be applied directly onto tissue. For example, one or more active agents may be deposited onto tissue to form a drug delivery patch. The tissue may be external or internal tissue. For example, the coating(s) may be applied onto internal tissues using a suitable endoscopic plasma device as discussed above. In other examples, the coating may be applied onto the external skin of a patient (such as, e.g., wounded tissue) and the active agent(s) allowed to diffuse into the tissue and thereby acts as a transdermal drug delivery system.

The coatings herein may comprise at least one biomolecule. For example, the coatings herein may comprise one or more proteins such as collagen, fibrin, and fibronectin; and/or biopolymers such as hyaluronan, chitosan, alginates, and cellulose. Additionally or alternatively, the coatings may comprise one or more other biomolecules such as phosphorylcholine, polypeptides, polyglycans, hormones, lipids, interferons, cartilage, therapeutic biologic agents both cellular and synthetically derived, autologous, homologous and allographic and zenographic biologic agents, autologous or homologous, recombinant and synthetic derived blood cells and products containing antimicrobial/antibiotic agents, bacteriostatic agents, stem cells, mesenchymal stem cells, amniotic membrane materials, fluorescein tagged collagen, bovine serum albumin, fibroblast derived Human Dermal Collagen, matrix proteins, fibrin, clotting factors, growth factors, or cytokines. The coatings may comprise mixtures of chemical and/or biological materials. In some examples, the biomolecule(s) do not contain vinyl groups or other chemical functionalities that would be expected to polymerize.

The coatings may comprise Type I, II, III, IV, V, VI or VII collagen or mixtures thereof. The coatings may be used to reduce scar formation, such as when the plasma treated collagen is applied directly to a cut, incision, or other wound. In at least one embodiment, the coating comprises collagen Type VII and is applied to treat epidermolysis bullosa patients.

In at least one embodiment, the coating may comprise autologous material applied to an implant or transplanted organ surface, e.g., to improve the biocompatibility and to reduce rejection of the implant or transplanted organ. The autologous material may be blood, platelet rich plasma, extracellular fluid, tissue (e.g., for tissue grafting), and/or other autologous materials.

In at least one embodiment, the coating may be deposited by dissolving a pharmaceutical agent in a solvent, nebulizing the solvent into a non-thermal atmospheric plasma, and depositing the resultant material as a dry coating on an adjacent substrate surface. In some aspects of the present disclosure, the active pharmaceutical does not contain any isolated vinyl or alkyne groups. However, the pharmaceutical active may contain aromatic unsaturation or conjugated vinyl groups that can be resonance stabilized. For example, resonance stabilized groups have been found to remain unreacted in the deposition and are not destroyed by the plasma. The pharmaceutical active agent may be deposited as a pure compound without the presence of polymers, binders, linkers, pre-treatments, biomolecules, excipients, or other materials. Thus, the coating may be formed of only the pharmaceutical agent and no other materials.

If prolonged elution is required, or if the pharmaceutical agent or biomolecule is particularly sensitive to active species within the plasma, then the active agent may be encapsulated within a microsphere. The microspheres may be prepared from a biocompatible drug delivery material including, but not limited to, proteins, polysaccharides, or liposomes. Microspheres may simultaneously protect the active agent from the more aggressive plasma species and/or may limit diffusion of the active agent from the surrounding material to provide for prolonged elution.

The average diameter of the microspheres may range from about 0.1 μm to about 500 μm, such as from about 0.1 μm to about 100 μm, from about 0.5 μm to about 100 μm, from about 1 μm to about 50 μm, from about 5 μm to about 10 μm, or from about 50 μm to about 250 μm. In at least one example, the microspheres suitable for drug delivery applications may have an average diameter ranging from 0.1 μm to 100 μm. Microspheres may be manufactured in a variety of ways including, e.g., emulsification polymerization, phase separation or precipitation and/or emulsion/solvent evaporation methods. Further, mechanical processes to produce microspheres include the air-suspension method, pan coating, spray drying, spray congealing, micro-orifice system and rotary fluidization bed granulator method.

In at least one embodiment, the coating contains only one or more pharmaceutically active agents, such as anti-cancer drugs (chemotherapy agents), anti-inflammatory drugs, immune-suppressants, antibiotics, analgesics, blood pressure medications, antithrombotics, anticoagulants, antiplatelet agents, thrombolytics, antiproliferatives, antimitotic, antimicrobial, agents that inhibit restenosis, smooth muscle cell inhibitors, fibrinolytic, immunosuppressive, and anti-antigenic agents, vaccines and combinations thereof. The coating may comprise one or more antibodies including endothelial progenitor cell antibodies or monocolonal antibodies. The monoclonal antibodies may be delivered directly onto a target tissue using a suitable plasma deposition device. This can then be used to provide targeted chemotherapy, radiotherapy or immunotherapy. For example, the presence of the antibody can stimulate the immune system to respond and thereby provide immunotherapy. For internal organs or targets, the coating may be deposited using an endoscopic or arthroscopic plasma device.

The elution of the active pharmaceutical may be tailored by increasing the degree of cross-linking or by choosing a hydrophobic material that has lower solubility in aqueous solution. The cross-linking can be enhanced by increasing the plasma power or increasing the contact time between the plasma and the coating. If desired, additional cross-linking can be provided by adding one or more chemical cross-linking agents. For example, hydrogen peroxide may be added. When exposed to the plasma, the hydrogen peroxide may produce additional free radicals within the mixture and can produce additional reactivity within the plasma, thereby producing enhanced cross-linking of the active agent(s). In order to prevent excess oxidation, the level of peroxide should be maintained below 3% by weight with respect to the total weight of the active agent(s). For example, the amount of hydrogen peroxide may range from about 0.1% to about 3.0% by weight, from about 0.5% to about 2% by weight, or from about 0.1% to about 1% by weight with respect to the total weight of the active agent(s). Peroxides and other molecules other than hydrogen peroxide can be used to enhance cross-linking. However, such other peroxides may leave residues in the coating that might alter biocompatibility.

According to some aspects of the present disclosure, the coating may comprise multiple layers. For example, a first layer of pharmaceutical agent (e.g., an antibiotic) may be applied to a surface using a plasma device as disclosed herein. The first layer may have a thickness ranging from about 50 nm to about 150 nm, such as from about 50 nm to about 75 nm, from about 75 nm to about 100 nm, or from about 100 nm to about 150 nm. Additional layers of the pharmaceutical agent may be deposited, e.g., by completing additional coating passes, each producing a further coating thickness ranging from 50 nm to 150 nm. Thus, for example, this method may be used to produce coating thicknesses of up to about 600 nm (e.g., 2, 3, or 4 or more first layers). On top of the first layer(s), one or more second layers (e.g., 2, 3, or 4 or more second layers) comprising one or more biomolecules may then be applied. Each second layer may have a thickness similar to the thickness of each first layer, e.g., ranging from 50 nm to 150 nm, providing for coating thicknesses of up to 1.2 µm. In some aspects of the present disclosure, the coating may comprise at least one first layer (comprising a pharmaceutical agent) between two second layers (comprising a biomolecule). In some aspects of the present disclosure, the coating may comprise at least one first layer (comprising a biomolecule) between two second layers (comprising a pharmaceutical agent).

In such examples comprising one or more first layers of a pharmaceutical agent and one or more second layers of biomolecules, the second layer(s) may reduce the elution rate of the pharmaceutical agent of the first layer(s) from the coating. For example, a single layer of protein may be applied to produce a second layer as a top coat having a thickness ranging from about 50 nm to about 150 nm of protein on top of the first layer(s) of pharmaceutical agent. Additional layers of protein (or other biomolecule(s)) may be added to increase the thickness of the top coating until the desired thickness is reached. For example, a top coat of 500 nm may be sufficient to slow elution of the pharmaceutical material of the first layer(s) to prolong release from the coating over multiple days. Thicker layers may be desired for pharmaceutical agents that are highly soluble (and thus more likely to be released from the coating more quickly). Thus, for example, the top coat may range from about 500 nm to about 900 nm, or from about 600 nm to about 800 nm. The combined thickness of the pharmaceutical first layers and the top coat of second layer(s) of biomolecules may range from about 200 nm to about 1500 nm. For example, the thickness of the total coating may be as thin as 200 nm, or may have a combined thickness ranging from 500 nm to 900 nm, or even a thickness up to 1500 nm. Some coatings having a thickness greater than 1500 nm tend to be brittle and may crack or delaminate.

Additionally or alternatively, elution of an active agent may be controlled by the degree of cross-linking of materials within the coating. For example, one or more layers comprising a pharmaceutical agent may be covered with one or more layers of cross-linked biomolecules. In at least one embodiment, the top layer(s) may comprise collagen and/or chitosan deposited using a plasma as discussed above. The degree of cross-linking in the protein deposited layer may be controlled, e.g., by adjusting the level of plasma power, adjusting the plasma exposure time, and/or adding one or more chemical cross-linkers. For example, protein coatings can be cross-linked using materials such as glutaraldehyde, formaldehyde, glyoxal or diisocyanate. A similar effect can be found by incorporating relatively low levels (e.g., less than 3%, less than 2%, or less than 1% by weight) of hydrogen peroxide into the active agent(s) to induce free radical reactions that produce additional reactivity in the plasma. These materials may act synergistically with the plasma to maximize cross-linking without exposing the protein to high levels of plasma energy. Alternatively, relatively low levels (e.g., less than 3%, less than 2%, or less than 1% by weight) of enzymatic cross-linkers such as transglutaminase can be premixed with the protein solution to produce a cross-linked thin film deposit. Increasing the thickness of the coating may produce slower breakdown of the coating in vivo and produce reduced elution of any material underneath by limiting diffusion through the coating.

Exemplary anticancer pharmaceutical agents (drugs) that can be deposited using these plasma processes include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene HCl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6, 4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

In at least one embodiment, the pharmaceutical agent (pharmaceutically active agent) is an anti-inflammatory drug selected from non-steroidal anti-inflammatory drugs, COX-2 inhibitors, glucocorticoids, and mixtures thereof. Exemplary non-steroidal anti-inflammatory drugs include aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone, acetaminophen, and mixtures thereof. Exemplary COX-2 inhibitors include nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof. Exemplary glucocorticoids include hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, and mixtures thereof.

Other exemplary pharmaceutical agents suitable for the present disclosure include cell cycle inhibitors in general, apoptosis-inducing agents, antiproliferative/antimitotic agents including natural products such as *vinca* alkaloids (e.g., vinblastine, vincristine, and vinorelbine), paclitaxel, colchicine, epidipodophyllotoxins (e.g., etoposide, teniposide), enzymes (e.g., L-asparaginase, which systemically metabolizes L-asparagine and deprives cells that do not have the capacity to synthesize their own asparagine); antiplatelet agents such as G(GP) $II_b/III_a$ inhibitors, GP-IIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), triazenes—dacarbazine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide; hormones (e.g., estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fluorocortisone, prednisone, prednisolone, 6α-methylprednisolone, triamcinolone, betamethasone, and dexamethasone), non-steroidal agents (salicylic acid derivatives e.g., aspirin; para-aminophenol derivatives e.g., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); antigenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retinoid; cyclin/CDK inhibitors; HMG co-enzyme reductase inhibitors (statins); and protease inhibitors (matrix protease inhibitors).

In at least one embodiment, the active agent(s) may include one or more antibiotics chosen from tobramycin, vancomycin, gentamicin, ampicillin, amoxiocillin, carbapenems, penicillin, chloramphenicol, cephalosporin C, cephalexin, cefaclor, cefamandole and ciprofloxacin, dactinomycin, actinomycin D, daunorubicin, doxorubicin, idarubicin, penicillins, piperacillin, streptomycin, cephalosporins, quinolones, anthracyclines, mitoxantrone, tetracyclines, ticarcillin, bleomycins, plicamycin (mithramycin), mitomycin, polymyxin, ciprofloxacin, glycopeptide and aminoglycan antibiotics and mixtures thereof.

In some embodiments, the active agent(s) may include one or more immunosuppressants, such as cyclosporine, rapamycin and tacrolimus (FK-506), ZoMaxx, everolimus, sirolimus, tacrolimus, zotarolimus, paclitaxel, etoposide, mitoxantrone, azathioprine, basiliximab, daclizumab, leflunomide, lymphocyte immune globulin, methotrexate, muromonab-CD3, mycophenolate, and thalidomide.

In some examples, the pharmaceutical agent(s) do not contain vinyl groups or other chemical functionalities that would be expected to polymerize.

In some embodiments, the active agent(s) (e.g., the coating precursor, pharmaceutical compound, or biomolecule) are not chemically modified to include extraneous reactive chemical functionalities.

The coatings disclosed herein may be applied to a medical device, e.g., to modify the surface of the medical device. For example, the coating may modify an implantable medical device. In some embodiments, the coating may increase the biocompatibility of the surface of the medical device by incorporating a biomolecule or other active agent that does not promote an inflammatory response. Additionally or alternatively, the coating may comprise a pharmaceutically active agent that inhibits inflammation, cell growth, cell attachment, and/or other biological process; and/or may inhibit bacterial and/or fungal growth. This may be achieved, for example, through the deposition of pharmaceutical agents including antibiotics and antifungals, or through the deposition of biomolecules such as antimicrobial peptides or combinations thereof. The medical devices may be constructed of metal, ceramic, plastic, carbon or combinations thereof, including composite materials. Non-limiting examples of metals and metal alloys include steel, titanium, titanium alloys including nitinol, cobalt chrome, gold, silver and platinum. Non-limiting examples of ceramics and glasses include alumina, zirconia, calcium phosphates, hydroxyapatite, and bioactive glasses such as 45S5. Non-limiting examples of polymers include polytetrafluoroethylene (PTFE), polyether ether ketone (PEEK), poly (methyl methacrylate), (PMMA), polyethylene (PE), silicones, hydrogels, and polyurethanes. Non-limiting examples of composites include PMMA-glass fillers, e.g., such as fillers used in dental restorations.

Examples of medical devices suitable for the present disclosure include, but are not limited to, scalpels, clamps, needles and medical implants such as stents, catheters, ports, expandable balloons, prosthetic implants, orthopedic implants, dental implants, cochlear implants, ear tubes, implantable mesh, spinal cages, maxillofacial implants, scaffolding (e.g., for tissue regeneration or grafting), pulse generators, valves, hormone delivery implants, skin grafts, bone grafts, artificial eye lenses, contact lens, hearing aids, breast implants, trauma fixation devices, screws, plates, rods, pins, nails, needles, biosensors, sensory implants, neural implants, pacemakers, defibrillators, electrodes, subcutaneous implants including drug delivery implants, cosmetic implants, hip implants and knee replacement implants, blood dialysis equipment and ventilators and associated tubes, valves and other components in contact with the air.

The coatings disclosed herein may be applied directly to a soft tissue surface, such as a wound. The deposited material may include materials to inhibit bacterial infection, stop bleeding, and/or promote healing. In an exemplary method, the plasma system or device is first used to induce hemostasis, reduce bacterial loading and treat the wound. In cases of high levels of bleeding, such as those encountered when operating on the liver, the hemostatic properties of the plasma can be enhanced by co-depositing materials that induce blood coagulation and minimize bleeding. Such hemostatic materials include clotting factors, fibrin, kaolin, hyaluronic acid, collagen, gelatin, epinephrine, thrombin and chitosan. The plasma may additionally or alternatively be used to ablate and/or incise unwanted tissue, reduce bacterial loading or to treat a tumour. Following this treatment of the wound, the plasma system or device may be used to deposit a coating that helps to repair or heal the tissue of the patient. The coating may comprise a pharmaceutical active, DNA or RNA, a protein or a polysaccharide or mixtures thereof. For example, a coating containing an anticancer drug may be deposited directly onto residual tumour cells or nearby tissue to deliver locally available anti-tumour effects. This may be achieved, for example, through topical deposition or via endoscopic delivery. When treating tumours or cancers, a nano-second or picosecond pulsed plasma may be used.

In a further example, wounded tissue may be treated with a combination of plasma and deposited material to enhance tissue regeneration. In this case, the coating may comprise materials such as collagen, hyaluronic acid, chitosan, and/or growth factors or other regenerative materials optionally alongside pharmaceutical agents designed to inhibit bacterial growth or to suppress pain. In at least one embodiment, the deposit comprises epithelial growth factor. In some embodiments, a sample of tissue may be treated with plasma and coated with one or more active agents before, during, or after using the sample of tissue in a tissue graft. Such tissue may comprise an autograft (e.g., a tissue sample from the same patient being treated), an allograft (e.g., a tissue sample from a person other than the patient), or a xenograft (e.g., a tissue sample from an animal).

In some embodiments, damaged tissue may be repaired through the insertion of an implant with at least one surface modified with a plasma deposited coating. For example, the implant may be a stent and the coating may be formed solely from an antiproliferative drug such as sirolimus, paclitaxel, everolimus, zotarolimus or biolimus. As the implant surface does not contain any polymers, linkers, binders or other excipients, the risk of late stage restenosis induced by the breakdown of foreign materials in the body is minimized, thereby favouring patient recovery. Optionally, the coating may contain materials such as heparin, phosphorylcholine or endothelial progenitor cell capture antibodies in addition to or in place of the pharmaceutical active.

In some embodiments, the methods disclosed herein may be used for agricultural purposes, e.g., with coatings applied to plants, seeds, fruits, vegetables, and/or other food products with materials that alter shelf life, size, appearance, and/or nutritional value.

In at least one embodiment, the active agent(s) are introduced downstream of the plasma. For example, the active agent(s) may be in indirect contact, rather than direct contact, with the higher energy region of the plasma, which is present inside the plasma chamber. By introducing the active agent(s) downstream or in the afterglow region, the degrading effects of the plasma may be minimized. In this region, outside of the plasma chamber and away from the electrodes, the glowing plasma generally is no longer present and only long-lived plasma species are present. In some embodiments, two or more active agents may be introduced to different regions of or near the plasma substantially simultaneously. As there are significantly fewer reactive species present, and the highly reactive species have quenched, the introduced materials undergo fewer reactions and participate only in lower energy reactions, thereby preserving the functionality of the active agents.

When mixtures of materials (biomolecules or pharmaceutical agents) are to be co-deposited, it may be found that one is relatively more reactive than the other, or that one is more prone to being denatured by the plasma. In this situation, the more robust or stable material may be introduced upstream of the less stable material. For example, the more robust or stable material may be introduced directly into the plasma and the less stable material may be introduced downstream of the plasma. This may ensure that the more robust material receives sufficient energy to initiate the cross-linking reactions, while the less stable material is introduced downstream and is shielded from the bulk of the more-reactive plasma species. Thus, both materials may react without one of them being denatured or otherwise deactivated. In an exemplary embodiment, the more robust material may be introduced into the plasma where it is activated. This plasma activated material is then allowed to exit the plasma and to react with a second, less stable material without any further meaningful contribution from plasma species. For example, if a coating was to be deposited which comprised a stable protein and a highly reactive pharmaceutical agent, the protein may be injected into the plasma and the pharmaceutical agent may be introduced downstream of the plasma. This could be achieved by injecting the protein directly into the plasma chamber and introducing the pharmaceutical into the afterglow which exists just outside the chamber. This may allow both materials to be sufficiently activated to crosslink on the target surface to produce a coating. Similarly, a coating comprising a relatively stable pharmaceutical agent and a less-stable biomolecule may be formed by injecting the pharmaceutical agent into the plasma and the biomolecule downstream of the plasma.

In an exemplary embodiment, a biomaterial and/or a pharmaceutical agent as the active agent(s) may be placed on the target substrate surface and then exposed to a plasma. The material(s) may comprise, for example, a biomolecule and/or a pharmaceutically active agent. The active agent(s) may be deposited as a layer less than 1 mm thick, such as less than 500 µm thick, e.g., less than 200 µm thick or less than 1 µm thick. The layer may be uniform across a portion of the substrate, or the entire substrate surface. The material(s) may be in liquid or gel solution, e.g., having been mixed with or dissolved in water or other solvent, or may be present as a dry powder. By exposing the material(s) to the plasma, the material(s) may be activated and cross-linked, and thereby converted into a coating. The plasma activation may also bind the material to the surface. In some embodiments, this method does not produce highly adherent coatings, for example, if the plasma does not directly activate the substrate surface due to the presence of the deposited layer which may act as a barrier. To address this issue, in some embodiments the substrate surface may first be activated using a plasma and the material(s) may then be applied as a thin layer. The biological or pharmaceutical activity of the active material(s) may be retained by use of a low energy, non-thermal plasma. In some embodiments, the plasma is pulsed. As discussed above, the target substrate surface may include surfaces that form part of a diagnostic component (e.g., multi-well plates and other components), a medical device (e.g., medical implants and other devices), or a wound (e.g., cuts, lesions, tumours, burns, and other wounds). In some embodiments, the precursor may be chosen from the group consisting of a protein, a peptide, an antibody, and a polysaccharide.

The following examples are intended to illustrate the present disclosure without, however, being limiting in nature. It is understood that the present disclosure encompasses additional embodiments consistent with the foregoing description and following examples.

EXAMPLES

Example 1. Antibiotic Coating of Steel Coupons

Metal coupons made from 304 stainless steel (10 mm diameter, 1 mm thickness) were cleaned in deionized water, acetone and again in water. After drying, a number of coupons were coated with gentamicin sulphate, a broad spectrum antibiotic, as follows.

A solution of gentamicin sulphate was prepared by dissolving the salt in water to yield a concentration of 50 mg/ml. This solution was then injected through a pneumatic nebulizer (T2100 nebuliser, Burgener Research Inc., Ontario, Canada) at a rate of 25 μL/min. This produced a consistent and stable spray of fine particles.

The nebulizer was then inserted to spray into a cylindrical plasma chamber (20 mm diameter, 45 mm in length). In addition, 6 L/min of helium (99% purity) was flowed through the chamber. Metal electrodes were inserted into the chamber and RF power was delivered using a Redline G2000 power supply. The outlet voltage was set to 135 V and a 45% duty cycle. This was fed to an external transformer that was connected directly to the electrodes. Upon turning on the power, the helium gas within the plasma chamber was ignited and formed a cold plasma.

The plasma was scanned over a sample holder which held the cleaned stainless steel coupons. The plasma was moved in a raster pattern at a speed of 15 mm/s and with a 3 mm step size. Each coupon was subjected to three coating passes on each side to give 6 layers of coating in total. A visible coating was evident on the surface of the steel samples after coating.

Example 2. Antimicrobial Properties of Coated Steel

The metal coupons of Example 1 coated with gentamicin were then analyzed for antimicrobial properties against a common bacteria—*Escherichia coli*: ATCC 8739 to determine if the antibiotic was still active.

Six gentamicin-coated coupons were individually placed into 10 ml of buffered sodium chloride peptone solution (BSCPS) and then inoculated with 1 ml of *Escherichia coli* stock. Six uncoated coupons were similarly placed in BSCPS and 1 ml of the *E. coli* inoculum to act as a control. Finally, 10 ml of BSCPS was inoculated with 1 ml of the bacterial stock and then immediately diluted and plated out to determine the initial bacterial cfu/ml. The samples were incubated at 30-35° C. for 24 hours and the coupons were then removed from incubation and the level of bacteria in each container were measured by serial dilution and plating out in duplicate. The results are shown in Table 1.

TABLE 1

| Sample | Average cfu | Log cfu |
|---|---|---|
| Initial inoculum | $1.1 \times 10^6$ | 6.04 |
| Uncoated sample after 24 hours | $7.2 \times 10^7$ | 7.85 |
| Gentamicin coated samples after 24 hours | $1.2 \times 10^5$ | 4.71 |

The results show an average 1.33 log reduction in counts obtained for *Escherichia coli* for the steel coupons coated with gentamicin, whereas the uncoated samples showed an average 1.81 log increase in bacterial counts. This confirms that the antibiotic is still active after deposition.

Other embodiments of the present disclosure will be apparent to those skilled in the art from consideration of the specification and practice of the embodiments disclosed herein. It is intended that the specification and examples be considered as exemplary only, with a true scope and spirit of the present disclosure being indicated by the following claims.

What is claimed is:

1. A method of producing a coated substrate, comprising:
introducing a plurality of dry particles as a dry powder into a non-thermal plasma, each particle comprising at least one active agent chosen from biomolecules, pharmaceutical agents, or combinations thereof, wherein the powder does not include hydroxyapatite, calcium phosphates, or other biominerals, the powder having a melting point of less than 100° C.; and
exposing a substrate to the plurality of dry particles and the plasma to deposit a continuous, dry coating comprising the at least one active agent onto the substrate in the absence of polymers, binders, linkers, and excipients.

2. The method of claim 1, wherein the coating consists of only the at least one active agent.

3. The method of claim 1, wherein the coating retains a biological or pharmaceutical activity of the at least one active agent.

4. The method of claim 1, wherein the substrate is chosen from tissue, a diagnostic component, a medical device, or a food product.

5. The method of claim 1, wherein the substrate comprises a multi-well plate and the at least one active agent comprises a biomolecule.

6. The method of claim 1, wherein the coating comprises at least one first layer comprising a pharmaceutical agent and at least one second layer comprising a biomolecule, and the at least one first layer is adjacent the at least one second layer.

7. The method of claim 6, wherein the biomolecule of the at least one second layer is cross-linked.

8. The method of claim 1, wherein the at least one active agent comprises a first active agent and a second active agent, and introducing the plurality of dry particles into the plasma comprises introducing the first active agent into a portion of the plasma downstream from a portion of the plasma into which the second active agent is introduced, wherein the first active agent is a biomolecule and the second active agent is a pharmaceutical agent.

9. The method of claim 1, wherein the plurality of dry particles is introduced into an afterglow region of the plasma.

10. A method of producing a coated substrate, comprising:
applying a plurality of dry particles comprising at least one active agent to a surface of a substrate by blowing gas through a permeable material containing the plurality of dry particles, the at least one active agent being chosen from biomolecules, pharmaceutical agents, or combinations thereof, wherein the permeable material comprises foam, mesh, or fabric; and
exposing the surface of the substrate to an afterglow of a plasma to form a dry coating comprising the at least one active agent in the absence of polymers, binders, linkers, and excipients.

11. The method of claim 10, wherein applying the at least one active agent includes forming a continuous, uniform layer of the at least one active agent on the surface of the substrate.

12. The method of claim 10, wherein the substrate is chosen from tissue, a diagnostic component, or a medical device.

13. The method of claim 10, wherein the dry coating retains a biological or pharmaceutical activity of the at least one active agent.

14. A method of producing a coated substrate, comprising:
exposing a substrate to a pharmaceutical agent and a plasma in the absence of polymers, binders, linkers, and excipients to deposit at least one first layer comprising the pharmaceutical agent onto the substrate, wherein the at least one first layer retains a pharmaceutical activity of the pharmaceutical agent; and
exposing the substrate to a biomolecule and the plasma to deposit at least one second layer comprising the biomolecule onto the at least one first layer of the substrate to form a coating, wherein the at least one second layer forms an outermost layer of the coating;
wherein the at least one first layer retains a pharmaceutical activity of the pharmaceutical agent, and the at least second layer retains a biological activity of the biomolecule, the at least one second layer reducing an elution rate of the pharmaceutical agent from the coating; and
wherein each of the pharmaceutical agent and the biomolecule is introduced into the plasma in the form of a powder that does not include hydroxyapatite, calcium phosphates, or other biominerals, each powder having a melting point of less than 100° C.

15. The method of claim 14, wherein the at least one first layer comprises a plurality of first layers having a total thickness ranging from 50 nm to 150 nm, the plurality of first layers consisting of the pharmaceutical agent.

16. The method of claim 14, wherein the substrate is chosen from tissue, a diagnostic component, or a medical device.

17. The method of claim 14, wherein the plasma has greater power during exposure of the substrate to the biomolecule and the plasma than during exposure of the substrate to the pharmaceutical agent and the plasma.

18. The method of claim 1, wherein the plasma is pulsed, the plasma delivering less than 100 W of power to the substrate.

19. The method of claim 1, wherein the dry powder is entrapped in or on a foam, mesh or fabric surface, and the plurality of particles is introduced into the plasma by blowing gas through the foam, mesh, or fabric.

20. The method of claim 1, wherein the at least one active agent has a Mohs hardness ranging from 1 to 3.

* * * * *